US008383341B2

(12) United States Patent
Manaresi et al.

(10) Patent No.: US 8,383,341 B2
(45) Date of Patent: Feb. 26, 2013

(54) METHOD FOR NON-INVASIVE PRENATAL DIAGNOSIS

(75) Inventors: Nicolò Manaresi, Milan (IT); Antonio Fittipaldi, Bologna (IT); Giuseppe Giorgini, Padova (IT); Gianni Medoro, Casalecchio di Reno (IT)

(73) Assignee: Silicon Biosystems S.p.A., Bologna (IT)

( * ) Notice: Subject to any disclaimer, the term of this patent is extended or adjusted under 35 U.S.C. 154(b) by 381 days.

(21) Appl. No.: 12/598,881

(22) PCT Filed: May 2, 2008

(86) PCT No.: PCT/IB2008/001083
§ 371 (c)(1),
(2), (4) Date: Mar. 8, 2010

(87) PCT Pub. No.: WO2008/135837
PCT Pub. Date: Nov. 13, 2008

(65) Prior Publication Data
US 2010/0196897 A1    Aug. 5, 2010

(30) Foreign Application Priority Data
May 4, 2007   (IT) .............................. TO2007A0307

(51) Int. Cl.
*C12Q 1/68* (2006.01)
*G01N 33/53* (2006.01)
(52) U.S. Cl. ............. 435/6.1; 435/4; 435/6.12; 435/7.1; 435/7.2; 435/7.21; 435/7.25; 435/287.2; 435/288.7
(58) Field of Classification Search .................. None
See application file for complete search history.

(56) References Cited

U.S. PATENT DOCUMENTS

| | | | |
|---|---|---|---|
| 2002/0006621 A1* | 1/2002 | Bianchi ............................. | 435/6 |
| 2003/0178309 A1* | 9/2003 | Huang et al. ................... | 204/547 |
| 2004/0072269 A1* | 4/2004 | Rao et al. ...................... | 435/7.23 |
| 2004/0091880 A1* | 5/2004 | Wiebusch et al. ................ | 435/6 |
| 2005/0069459 A1* | 3/2005 | Ahn et al. ...................... | 422/100 |
| 2005/0081429 A1 | 4/2005 | Ren et al. | |
| 2005/0181429 A1 | 8/2005 | Fejgin et al. | |
| 2005/0214173 A1* | 9/2005 | Facer et al. ................... | 422/100 |
| 2006/0051775 A1 | 3/2006 | Bianchi | |
| 2006/0134599 A1* | 6/2006 | Toner et al. ....................... | 435/4 |

FOREIGN PATENT DOCUMENTS

| | | |
|---|---|---|
| EP | 1439897 A2 | 7/2004 |
| WO | WO-00/69565 A1 | 11/2000 |
| WO | WO-02/077269 A1 | 10/2002 |
| WO | WO-2007010367 A9 | 6/2007 |
| WO | WO-2007107830 A1 | 9/2007 |
| WO | WO-2007110739 A3 | 2/2008 |
| WO | WO-2007116312 A8 | 11/2008 |

OTHER PUBLICATIONS

Borgatti et al., *International Journal of Molecular Medicine*, 21:3-12 (2008).
International Search Report in PCT/IB2008/001083 dated Oct. 28, 2008.
Nagy et al., *Prenat Diagn*. 25:398-402 (2005).
Xu et al., *Journal of Physics*, 34:1106-1111 (2006).
Nagy et al., "Isolation of epsilon-haemoglobin-chain positive fetal cells with micromanipulation for prenatal diagnosis", *Prenat Diagn* 25:398-402 (2005).
Adinolfi et al., Detection of trisomy 18 and Y-derived sequences in fetal nucleated cells obtained by transcervical flushing, Lancet, 342(8868):403-4 (1993).
Adinolfi et al., First trimester prenatal diagnosis using transcervical cells: an evaluation, Hum. Reprod. Update, 3(4):383-92 (1997).
Adinolfi et al., Rapid detection of aneuploidies by microsatellite and the quantitative fluorescent polymerase chain reaction, Prenat. Diagn., 17(13):1299-311 (1997).
Bianchi et al., Detection of fetal cells with 47,XY,+21 karyotype in maternal peripheral blood, Hum. Genet., 90(4):368-70 (1992).
Bianchi et al., Development of a model system to compare cell separation methods for the isolation of fetal cells from maternal blood, Prenat. Diagn., 16(4):289-98 (1996).
Bianchi et al., Fetal cells in maternal blood: determination of purity and yield by quantitative polymerase chain reaction, Am. J. Obstet. Gynecol., 171(4):922-6 (1994).
Bianchi et al., Fetal gender and aneuploidy detection using fetal cells in maternal blood: analysis of NIFTY I data. National Institute of Child Health and Development Fetal Cell Isolation Study, Prenat. Diagn., 22(7):609-15 (2002).
Bianchi et al., Possible effect of gestational age on the detection of fetal nucleated erythrocytes in maternal blood, Prenat. Diagn., 11(8):523-8 (1991).
Bianchi et al., Transferrin receptor (CD71) expression on circulating mononuclear cells during pregnancy, Am. J. Obstet. Gynecol., 170(1 Pt 1):202-6 (1994).
Bussani et al., Use of the quantitative fluorescent-PCR assay in the study of fetal DNA from micromanipulated transcervical samples, Mol. Diagn, 8 (4) 259-263, 2004.
Bussani et al., Strategies for the isolation and detection of fetal cells in transcervical samples, Prenat. Diagn., 22(12):1098-101 (2002).

(Continued)

*Primary Examiner* — Carla Myers
(74) *Attorney, Agent, or Firm* — Marshall, Gerstein & Borun LLP

(57) ABSTRACT

Method for non-invasive prenatal diagnosis comprising the following steps: a. obtain a sample of an organic fluid having a high probability of containing foetal cells from a pregnant woman; b. enrich said sample of organic fluid in at least one population of cells comprising at least one type of foetal nucleated cells; c. isolate at least one cell from among said at least one type of foetal nucleated cells; d. perform a genetic analysis on said at least one cell isolated from among said at least one type of foetal nucleated cells in order to highlight at least one genetic characteristic of said at least one foetal nucleated cell suitable for permitting said diagnosis; wherein the step of isolating at least one cell from among said at least one type of foetal nucleated cells is performed by individually selecting single cells in a microfluidic device designed for said purpose.

20 Claims, 5 Drawing Sheets

OTHER PUBLICATIONS

DeMaria et al., Improved fetal nucleated erythrocyte sorting purity using Intracellular antifetal hemoglobin and Hoechst 33342, Cytometry, 25(1):37-45 (1996).

Enger et al., Optical Tweezers applied to a microfluidic system, Lab Chip 4: 196-200 (2004).

Fiedler et al., Dielectrophoretic sorting of particles and cells in a microsystem, Anal. Chem., 70(9):1909-15 (1998).

Geifman-Holtzman et al., Fetal RhD genotyping in fetal cells flow sorted from maternal blood, Am. J. Obstet. Gynecol., 174(3):818-22 (1996).

Hulten et al., Rapid and simple prenatal diagnosis of common chromosome disorders: advantages and disadvantages of the molecular methods FISH and QF-PCR, Reproduction, 126(3):279-97 (2003).

International Preliminary Report on Patentability for PCT/IB2008/001083, dated Aug. 7, 2009.

Leung et al., Rapid anueoploidy screening (FISH or QF-PCR): the changing scene in prenatal diagnosis?, Expert. Rev. Mol. Diagn., 4(3):333-7 (2004).

Manaresi et al., A CMOS chip for individual cell manipulation and detection, IEEE J. Solid-State Circuits, 38(12):2297-305 (2003).

Miller et al., Transcervical recovery of fetal cells from the lower uterine pole: reliability of recovery and histological/immunocytochemical analysis of recovered cell populations, Hum. Reprod., 14(2):521-31 (1999).

Nicolini et al., The introduction of QF-PCR in prenatal diagnosis of foetal aneuploidies: time for reconsideration, Hum. Reprod. Update, 10(6):541-8 (2004).

Reichle et al., Combined laser tweezers and dielectric field cage for the analysis of receptor-ligand interactions on single cells, Electrophoresis, 22(2):272-82 (2001).

Romani et al., Proceedings of the International Solid State Circuit Conference, 1:224-5 (2004).

Samura et al., Comparison of fetal cell recovery from maternal blood using a high density gradient for the initial separation step: 1.090 versus 1.119 g/ml, Prenat. Diagn., 20(4):281-6 (2000).

Sekizawa et al., Fetal cell recycling: diagnosis of gender and RhD genotype in the same fetal cell retrieved from maternal blood, Am. J. Obstet. Gynecol., 181(5 Pt. 1):1237-42 (1999).

Sekizawa et al., Improvement of fetal cell recovery from maternal blood: suitable density gradient for FACS separation, Fetal Diagn. Ther., 14(4):229-33 (1999).

Shettles, Use of the Y chromosome in prenatal sex determination, Nature, 230(5288):52-3 (1971).

Van Zwieten et al., How unexpected are unexpected findings in prenatal cytogenetic diagnosis? A literature review, Eur. J. Obstet. Gynecol. Reprod. Biol., 120(1):15-21 (2005).

Wang et al., Fetal nucleated erythrocyte recovery: fluorescence activated cell sorting-based positive selection using anti-gamma globin versus magnetic activated cell sorting using anti-CD45 depletion and anti-gamma globin positive selection, Cytometry, 39(3):224-30 (2000).

Zheng et al., Demonstration of spontaneously dividing male fetal cells in maternal blood by negative magnetic cell sorting and fish, Prenat. Diagn., 15(6):573-8 (1995).

Zheng et al., Flow sorting of fetal erythroblasts using intracytoplasmic anti-fetal haemoglobin: preliminary observations on maternal samples, Prenat. Diagn., 15(10):897-905 (1995).

Zheng et al., Search for the optimal fetal cell antibody: results of immunophenotyping studies using flow cytometry, Hum. Genet., 100(1):35-42 (1997).

* cited by examiner

D18S535

METHOD FOR NON-INVASIVE PRENATAL DIAGNOSIS

CROSS-REFERENCE TO RELATED APPLICATIONS

This is the U.S. national phase application of PCT/IB2008/001083, filed May 2, 2008, which claims the benefit of Italian patent application No. TO 2007A000307, filed May 4, 2007.

TECHNICAL FIELD

The present invention concerns methods for non-invasive prenatal diagnosis, in particular for the identification of genetic and chromosomic disorders in the foetus.

STATE OF THE ART

Prenatal diagnosis for chromosomic disorders was introduced with the aim of highlighting abnormalities of the chromosomes in the foetus.

So far, the diagnostic certainty of a foetus being affected by a chromosome disorder can be obtained only by means of invasive diagnostic tests, examining the embryonic cells in order to determine the karyotype by means of amniocentesis, sampling of the chorionic villi or cordocentesis.

All these tests are invasive and involve an increased risk of miscarriage. They are therefore usually recommended for women over the age of 35, or women who in a previous pregnancy have had a child affected by chromosome disorders or when ultrasound scanning identifies a foetus with a malformation.

The discovery of the existence of foetal cells, although rare, in the maternal circulation has led many groups to research and develop methods for the isolation and recovery of said cells which permit non-invasive prenatal diagnosis. In particular, there are three main types of foetal cells able to pass through the placental barrier: lymphocytes, trophoblasts and erythroblasts. Of these, research has been directed above all at studying methods for the isolation of foetal erythroblasts from the peripheral maternal blood and trophoblasts, epithelial cells deriving from the placenta. Isolation of the trophoblasts from the peripheral blood is limited by their multinucleate morphology, whereas it has been demonstrated [8-13] that these cells are present, between the 6th and 15th week of gestation, in transcervical samples. It should be noted that the trophoblasts which migrate from the placenta often adhere to other trophoblasts or maternal cells forming clumps.

The identification of foetal cells has also recently been made possible by molecular biology methods applied directly to non-cultivated foetal cells. Said methods are for example prenatal FISH (Fluorescent In Situ Hybridization) and Quantitative Fluorescent-Polymerase Chain Reaction (QF-PCR). QF-PCR is a method able to identify and simultaneously quantify chromosome-specific DNA sequences which, being applicable to individual cells, has permitted genetic analysis on the basis of a very low number of foetal cells. In literature there are numerous publications including some reviews [1-6, see References at the end of the description], the content of which is incorporated here for the parts necessary for simple reference, concerning the use of QF-PCR in prenatal analyses.

D. W. Bianchi and colleagues developed [14-27] a system of isolation of the foetal nucleated erythrocytes (NRBCs) from maternal blood based on multiparametric scoring; the parameters include two morphological characteristics (roundness and morphology of the nucleus) and two properties of the foetal haemoglobin marking (fluorescence intensity and peripheral luminosity of the cytoplasm). The protocol provides for separation of the mononucleated cells on density gradient and enrichment by depletion of leukocytes (MACS with antibodies for CD15 and CD45) and isolation on cytofluorimeter with FACS method using a gamma anti-haemoglobin antibody. The cells identified via the multiparametric scoring are recovered using a micromanipulator under microscopic observation.

The scoring system is very laborious and use of the micromanipulator causes the loss of part of the cells. In general this method has shown a 74% sensitivity in the recovery of foetal cells combined with a frequency of false positives of 5%.

Separation of the mononucleated cells on density gradient and enrichment of the sample by MACS with depletion of CD71+ cells, further marked with specific antibodies for the gamma and epsilon foetal haemoglobin chains, is also known from other works [7]. Said marking can, however, produce aspecifics, as there are cases of production of foetal haemoglobin in adult cells, or due to the cross-link between the antibody for the foetal haemoglobin and the adult haemoglobin, caused by the similarity of these haemoglobin chains.

MonaLiza Medical Ltd. (US patent 2005/0181429 A1) developed a prenatal genetic analysis method using transcervical cells. The method is based on the use of a Pap smear cytobrush for the recovery of transcervical samples, which are processed by means of cytocentrifugation for the preparation of slides. The transcervical cells are marked and analysed under the microscope and their location and coordinates on the slide are memorised. The slide is analysed in FISH and the trophoblastic cells are identified using the coordinates obtained previously. The disadvantage of said method is that during the processing for preparation of the slide, part of the transcervical cells are lost, with a no-call due to lack of trophoblasts.

AVIVA-Biosciences Corporation (see for example EP-A-1439897) developed a system of enrichment based on biochips to isolate foetal cells from maternal blood. This method uses a reagent which permits removal of the majority of the erythrocytes, sorting by means of highly specific magnetic beads and a cocktail of specific antibodies for foetal antigens and enrichment by means of high resolution filtering chambers with pores having variable diameter according to the type of cells to be isolated.

Said method, however, is confined to the selection of foetal cells by means of enrichment of the sample, which does not limit the possibility of having contaminating maternal cells and therefore the consequent risk of an unreliable genetic analysis.

In short, none of the above-mentioned non-invasive methods has so far demonstrated that it can be used as a routine practice for the diagnosis of foetal aneuploidies and/or other chromosome defects.

The aim of the present invention is therefore to provide a method for non-invasive prenatal diagnosis, based on the sampling of an organic maternal fluid, with high probability of containing circulating foetal nucleated cells and their subsequent isolation, in particular a uterine, endocervical or transcervical fluid, or peripheral maternal blood. A further aim of the present invention is to provide a method for prenatal diagnosis that can be automated, without false negatives, and with a low number of false positives and no-calls.

SUMMARY OF THE INVENTION

The present invention concerns methods and devices for non-invasive prenatal diagnosis, in particular for the identification of genetic abnormalities in the foetus.

According to the present invention, therefore, the diagnosis is performed on the basis of an organic maternal fluid with high probability of containing foetal nucleated cells and the subsequent isolation thereof, in particular from a uterine, endocervical or transcervical fluid or peripheral maternal blood, identifying and analysing the foetal cells present in it, proceeding according to the method of claim 1.

According to the present invention, the uterine, endocervical or transcervical fluid or the peripheral maternal blood is firstly processed via one or more enrichment stages of the foetal nucleated cells. The method is characterised by the use of a microfluidic system able to individually select, in an easily automatable and repeatable way, single cells from the enriched sample. By means of a microfluidic system of isolation of single cells, it is possible to obtain a set of foetal cells with purity sufficient to perform a genetic diagnosis.

By microfluidic device we mean a device suitable for managing volumes of liquid with a laminar flow.

By microfluidic device we furthermore mean a device which has at least one dimension smaller than 1 mm.

By device able to individually select single cells we mean a device able to perform the selection of one or more single cells, one at a time or simultaneously, on the basis of parameters assessed individually on each cell.

The genetic analysis can then be performed via techniques such as Quantitative Fluorescent PCR (QF-PCR), if necessary using analysis of the cells of the mother for the comparison, FISH, karyotype or Comparative Genomic Hybridization (CGH).

The use of a microfluidic system offers various advantages including the possibility of having disposable systems, without risks of contamination between the different analyses or the need for thorough washing of the equipment. Furthermore the use of a microfluidic system offers the possibility of having automatic or semiautomatic systems, characterised by a high level of reliability.

Further characteristics and advantages of the invention will appear clear from the following description of some non-limiting implementation examples, with reference to the figures of the accompanying drawings.

DETAILED DISCLOSURE

Figure 1:
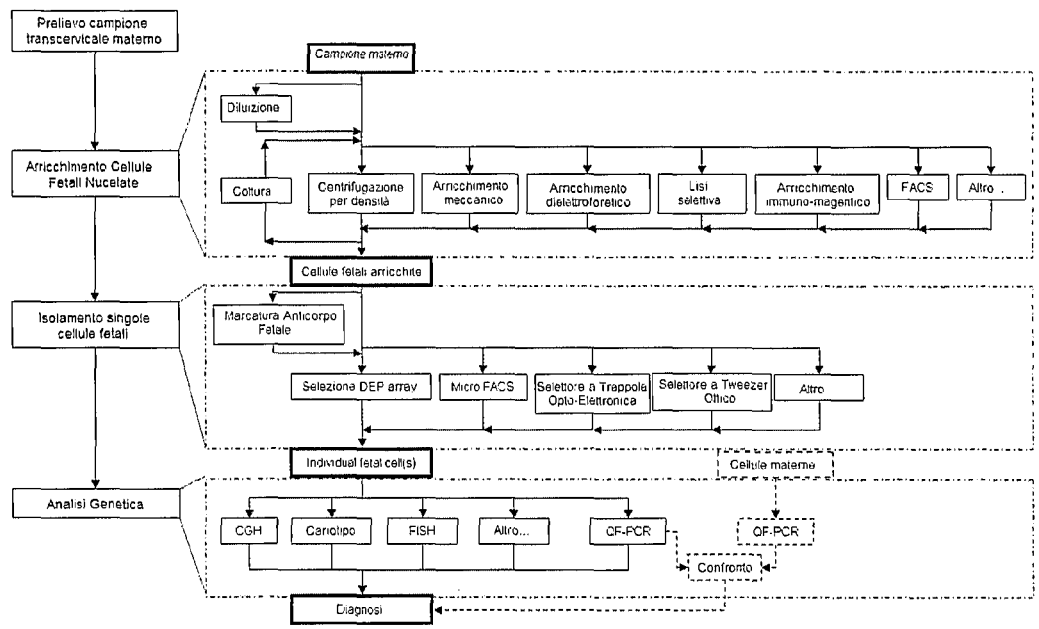
FIG. 1 shows a summary diagram of the non-invasive prenatal diagnosis method according to the present invention.

The subject of the present invention is a method for performing non-invasive prenatal diagnosis.

Collection of Transcervical Samples

The transcervical samples (TCC) can be taken from different levels of the uterus (external bone, lower part of cervical canal, lower uterine pole, intrauterine cavity) by means of various techniques: aspiration of the cervical mucus, cytobrush or swab, endocervical lavage and intrauterine lavage (IUL).

Enrichment Starting from Peripheral Blood

The proportion of foetal cells can be enriched using various methods, for example centrifugation on density gradient, consisting of solutions such as Ficoll or Percoll; mechanical enrichment, based on microfabricated filters which select nRBC and empty the sample of RBC; enrichment via dielectrophoretic separation by means of a specific device, the Dielectrophoretic activated cell sorter (DACS); selective lysis, for example selective lysis of the erythrocytes of no interest; immunomagnetic separation, by means of immunomagnetic beads with positive selection (using beads linked to specific antibodies for the foetal population to be recovered) or negative selection (depletion of cellular populations of no interest), and in which the two types of selection can be coupled to increase the specificity of the method (as, for example, in US2006/0051775—Bianchi); FACS, on cells marked with specific fluorescent antibody for foetal antigens.

The majority of these methods are also automated and all the separation methods can be preceded by separation of total mononucleated cells by means of centrifugation on density gradient or alternatively they can be applied on blood in toto.

In general the process starts from a dilution, but it is not strictly necessary for all the techniques.

Other Enrichment Techniques

A further technique well known to persons skilled in the art is called MACS by Miltenyi Biotech, or Easy-sep by Stemcell technologies.

To summarise, considering the case of organic fluid consisting of peripheral maternal blood, enrichment of the blood sample in the population of cells comprising at least one type of foetal cells can be obtained via a process in successive phases with, for example, a first phase in which total mononucleated cells are separated from the maternal sample, previously diluted in PBS/EDTA by means of Ficoll density gradient centrifugation. Obviously, as an alternative, any one of the other methods summarised in FIG. 1 could be used, for example enriching of the maternal sample via a selection of cells made on the basis of at least one parameter chosen from the group consisting of:
a. density;
b. morphology;
c. electrical properties;
d. chemical properties;
e. mechanical properties;
f. expression of surface antigens;
g. expression of intra-cytoplasmatic antigens;
h. dielectric properties;
i. magnetic properties;
or combinations of the same.

Subsequently enrichment of the foetal cells is further obtained by means of a second phase in which the positive or negative selection of cells is made, for example expressing the CD71, from the mononucleated cells recovered in the first step. Obviously the second enrichment step can comprise a selection made on the basis of at least one of the following characteristics of the population of cells comprising at least one type of foetal nucleated cells:
a. express the CD71 surface antigen (as already described and which represents the preferred form of the invention);
b. express the CD34 surface antigen;
c. express the GPA surface antigen;
d. not express the CD14 surface antigen;
e. not express the CD15 surface antigen;
f. not express the CD45 surface antigen.

Furthermore said second phase of enriching the sample in the population of cells comprising at least one type of cells can be performed via one of the following techniques:
a. MACS or Magnetic Activated Cell Sorter;
b. DACS or Dielectrophoretic Activated Cell Sorter;
c. FACS or Fluorescence Activated Cell Sorter.

Marking of the Foetal Cells
Immunostaining of Trophoblasts

If the sample is a TCC sample, before marking, the sample is incubated with acetyl-cysteine and agitated vigorously to dissolve the clumps and obtain a suspension of single cells.

For identification of the foetal cells, a marking with a specific antibody for the foetal cells (able to discriminate them from the maternal ones) is used, proceeding as in the known art. The trophoblasts can be marked using a variety of antibodies directed against specific antigens:
HLA-G, NDOG-5, BC1, Factor XIII, FDO202N, JunD, Fra2, HASH2 and PP5 (placental protein), specific for the extravillous trophoblasts;
FT1.41.1, I03, NDOG-1 and AB-154, specific for the syncytium trophoblasts;
CK-7 (cytokeratin-7), CHL1 (CD146), CHL2, H315, HLA-C, aHCG, IGF-II, PAI-1 and p57, expressed on the trophoblasts;
PLAP (placental alkaline phosphatase), AB-340 and D6, expressed on syncytium trophoblasts and cytotrophoblasts;
Tapasin and CAR, specific for invasive or extravillous but not villous trophoblasts;
PLAC1, PLAC4, PLAC8 and PLAC9, placental specifics, in particular of the trophoblast lineage cells;
PAR-1 (protease activated receptor), expressed on placental cells from the 7th to the 10th week of gestation;
GLUT-12 (glucose transporter protein), expressed on syncytium trophoblasts and extravillous trophoblasts from the 10th to the 12th week of gestation;
NDPK-A (nucleoside diphosphate kinase A), expressed on extravillous trophoblasts during the first three months of pregnancy.

Immunostaining of Erythroblasts from Samples of Peripheral Maternal Blood

For identification of the foetal cells, a marking with a second specific antibody for the foetal cells (able to discriminate them from the maternal ones) is used, different from the antibody used for the enrichment which, as described above, is not necessarily specific for the foetal cells.

In this case the following can be used:
antibodies that recognise surface antigens (like i-antigens);
intra-cellular antigens (for example, the globin chains γ or ε. In these cases the cells are preferably fixed and permeabilised, as in the known art, to permit good marking.

It should be noted that although from previous studies use of the anti-i-antigen antibody to mark foetal cells is known, said antibody was used directly in a device based on density gradient. Marking of the foetal cells by means of i-antigen antibody preceded by enrichment of the CD71+ cells has the advantage of performing a pre-selection of the foetal cells (sample enriched in foetal erythroblasts) and facilitating identification of the cells of interest, furthermore obtaining a very sensitive and specific marking.

Cells Already Marked

The foetal cells can be already marked if an antibody which is specific for the foetal cells (able to discriminate them from the maternal ones) and is fluorescent or conjugated with a fluorescent bead or conjugated with a fluorescent secondary or tertiary antibody has been used in the enrichment. In this case the enriched sample can be injected directly into the microfluidic device able to select single cells, since it is already possible to identify the foetal cells.

Isolation of Single Foetal Cells

Subsequently, the sample containing the cells is placed in a microfluidic device able to individually select single cells, of any known type. For said purpose a dielectrophoretic isolation can be used (DEPArray, using for example the techniques described in PCT/IB2007/000963 or in PCT/IB2007/000751, or [31] and [32]), or opto-electronic traps or optophoretic isolation or laser tweezers [28-30]. The content of said documents [28-30] and [31-32] is incorporated here for the parts necessary for simple reference.

Identification of the cells of interest can be performed for example by sensors:
external
optical such as a fluorescence microscope, or also
internal
optical, as illustrated in the patents PCT/IB2006/000636 and WO2007010367, which describe an integrated method of identification of the fluorescent cells
impedentiometric, as illustrated in the patents PCT/IB2006/000636 and WO2007010367 to identify dielectric beads associated with cells.

Genetic Analysis

Various types of analysis can be performed on the foetal cells recovered permitting genetic or chromosomic characterisation at different levels of resolution and sensitivity and according to the diagnostic purpose of the study.

In the event of supposed chromosome disorders, analysis of the karyotype with classic or molecular method (FISH) or the study of chromosome markers by means of QF-PCR can be performed. The acquisition or loss of genetic material can also be investigated by means of Comparative Genomic Hybridization.

Examples of Preferential Embodiments of the Invention

Figure 8:
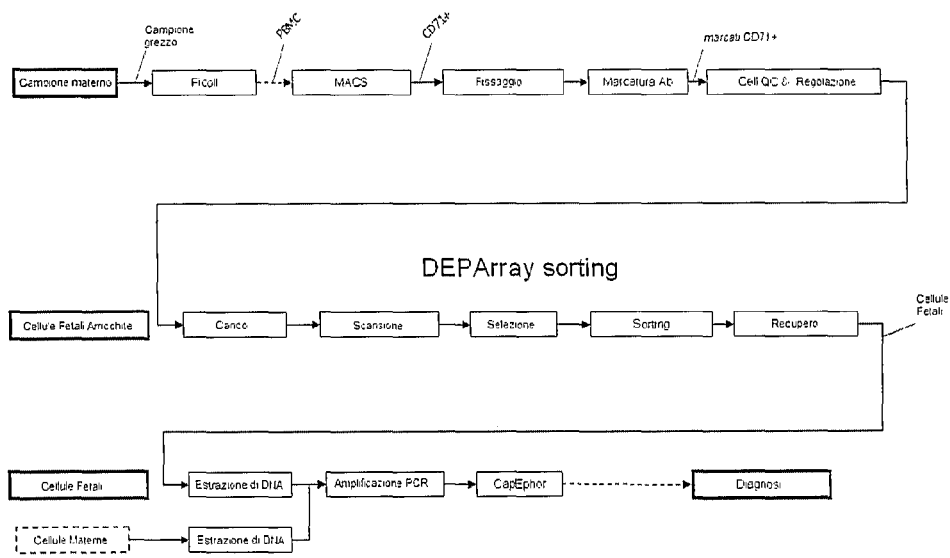
FIG. 8 shows a flow chart of a preferred embodiment of the method according to the present invention.

By way of non-limiting example of the object of the invention, a preferential embodiment of the method according to the present invention is given, following the flow chart indicated in FIG. 8.

Collection of Sample 10 ml of peripheral blood are taken from a pregnant woman.

Enrichment

The preferred embodiment of the invention comprises a process in successive phases having a first phase in which total monoucleated cells are separated from the maternal sample.

Said phase comprises a 1:1 dilution of the maternal blood with PBS pH 7.2. The sample diluted is then stratified on a single Ficoll gradient 1.077 g/ml and centrifuged at a speed of 300 g for 30 min at 22° C. The ring of cells that has accumulated above the Ficoll is collected and transferred to a sterile test tube.

According to a characteristic of the present invention, a part of the blood or mononucleated cells is not further processed and is used for analysis of the maternal DNA.

Enrichment of the foetal nucleated cells is then further obtained via a second phase, in which cells expressing the CD71 are positively selected from the mononucleated cells recovered in the first step. The positive selection is performed by means of immunomagnetic separation (MACS—Miltenyi Biotec) with the use of anti-CD71 antibodies conjugated with magnetic beads.

For the immunomagnetic separation, the cells are re-suspended in 80 µl of PBS every $10^7$ cells and then 20 µl of anti-CD71 micro-beads (Miltenyi Biotec) are added every $10^7$ cells. After an incubation of 15 min at 4° C., the cells are passed through a column connected to a magnetic field which retains the positive CD71 cells. The cells retained are then eluted from the column and used for the subsequent phase.

Isolation

The CD71+ cells (positive for CD71) thus obtained are fixed with formaldehyde 3.7% for 15 min at 22° C. The cells fixed are then permeabilised with a solution of NP-40 (Sigma Aldrich) 0.1% in PBS. An antibody (1 µg/ml) which recognises the gamma chain of the foetal hemoglobin conjugated with the fluorochrome FITC is added to the permeabilised cells.

According to an important aspect of the invention, the sample is furthermore, in combination, countermarked with DAPI (or other suitable marker) to show the nuclei of all the cells.

Before being loaded in the chip for dielectrophoretic manipulation and isolation of the foetal cells, the sample undergoes a quality control to verify the fluorescence intensity of the marking and the total cellular content. A portion of the marked sample is re-suspended in a minimum specific buffer volume useful for the dielectrophoretic manipulation and is loaded in a device for quality control of the sample and examined under the fluorescence microscope: the fluorescence intensity of the cells is observed in the various channels and a count is performed of the cells marked in DAPI (total nucleated cells). If the cellular concentration is above the optimal concentration for correct operation of the device for isolation of the single cells, the sample is diluted to obtain the required concentration; if the total number of cells is too low to allow the recovery of a minimum number of foetal cells, the foetal cells are not recovered (no-call result).

For calculation of the optimal concentration of cells we refer to a specific commercial device (DEPArray™, Silicon Biosystems SpA), WO0069565, based on mobile dielectrophoresis cages, in particular the model CONV600k comprising 100,000 cages.

A preferential method of use of said device provides for the following steps:

1. Select the cages containing a foetal cell (positive to marking).
2. If the cell is part of a cluster, i.e. it shares the cage with other non-foetal cells, divide the cells of the cluster into separate cages until the foetal cell is isolated in a cage not shared with other non-foetal cells. If the foetal cell does not separate from the other non-foetal cells, discard it.
3. Recover all the foetal cells in one single cage.

A further alternative preferential method of use of said device provides for the following steps:

1. Select the cages containing a foetal cell (positive to the marking).
2. If the cell is part of a cluster, discard it from the list of cells to be recovered.
3. Recover all the foetal cells in a single cage.

In this second case, the choice of the mean density of cells per cage (ACPC) to be injected in the chip is made taking account of the number of total cells present in the sample (NCELLSTOT) and the expected percentage of foetal cells (PCI).

Figure 9:
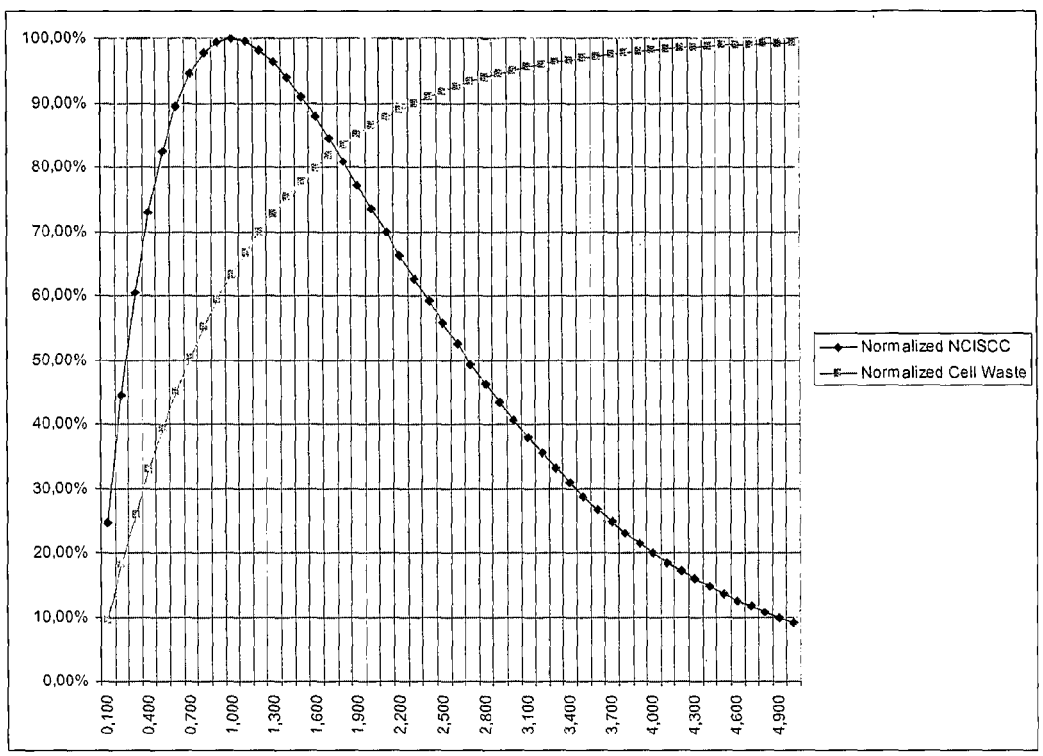
FIG. 9 shows the trend of the number of foetal cells in a single cage (NCISCC) according to the mean density of cells per cage (ACPC).

In fact, when the ACPC increases, the number of foetal cells present in the manipulation chamber of the chip increases. However, the probability of each cell belonging to a cage with single cell decreases, and the number of foetal cells in a single cage (NCISCC) therefore reaches a maximum for ACPC~=1. Said value is independent of PCI, and can be defined a normalised value of NCISCC with respect to the theoretical maximum for ACPC=1, the trend of which is shown in the graph of FIG. 9. Said concentration maximises the number of cells that can be recovered at each flushing of sample into the manipulation microchamber. This is a good choice if the total number of foetal cells that can be recovered is sufficient for the genetic analysis downstream.

As ACPC increases, there is a growing monotonic increase in the percentage of cells to be discarded due to the fact that they share the cage with other non-foetal cells, as illustrated in FIG. 9 in reference to the normalised value with respect to the number of foetal cells present in the manipulation microchamber (normalized cell-waste).

If the number of recoverable cells is below the minimum required for the analysis downstream, the sample can be diluted and a greater number of flushings performed to recover a greater number of foetal cells.

The optimal ACPC value to recover a sufficient number of foetal cells with the lesser number of flushings can be calculated on the basis of the statistical analysis determined above, for example with calculations based on the expected number of foetal cells and the minimum number of cells for the genetic analysis, therefore identifying a minimum recovery efficiency (ratio between cells in single cage/cells in cage with other cells) of the foetal cells present in the sample. From said efficiency a maximum value of ACPC can be deduced, hence a minimum number of flushings to process the entire sample with said recovery efficiency.

Figure 10:
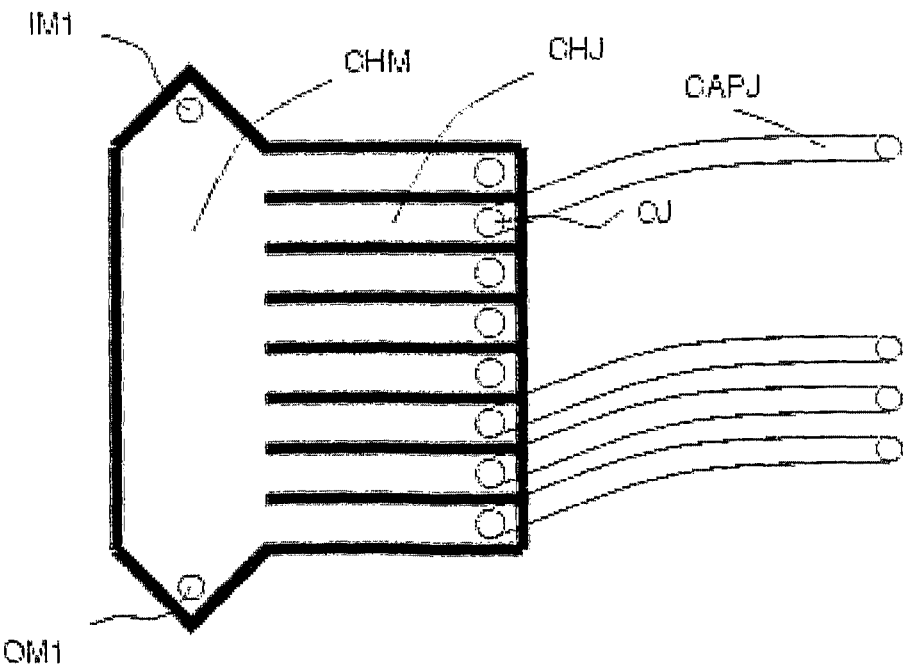
FIG. 10 shows schematically an example of a device for implementation of the method (or of the substantial and characterising part of it) according to the invention.
Figure 1:
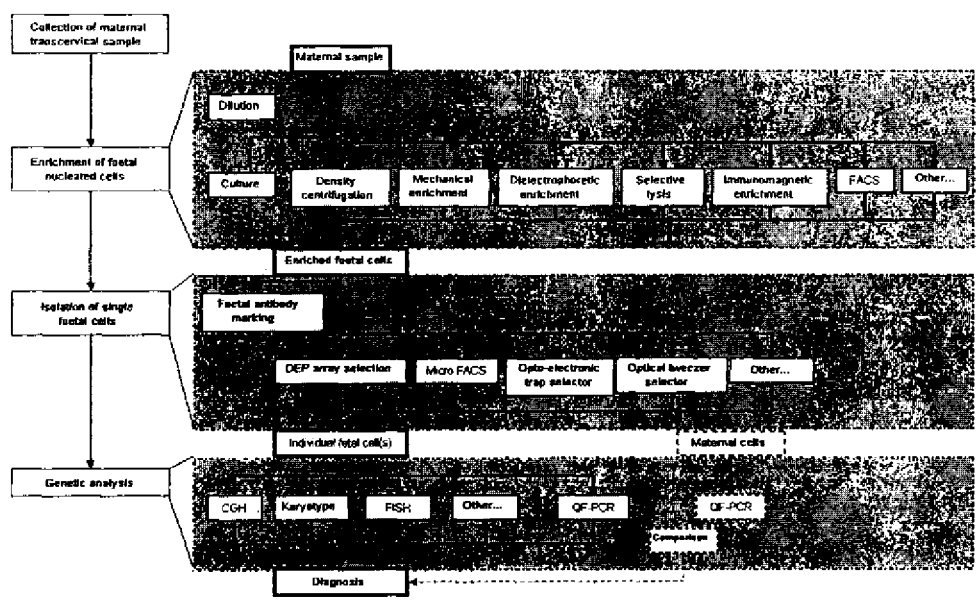
Figure 8:
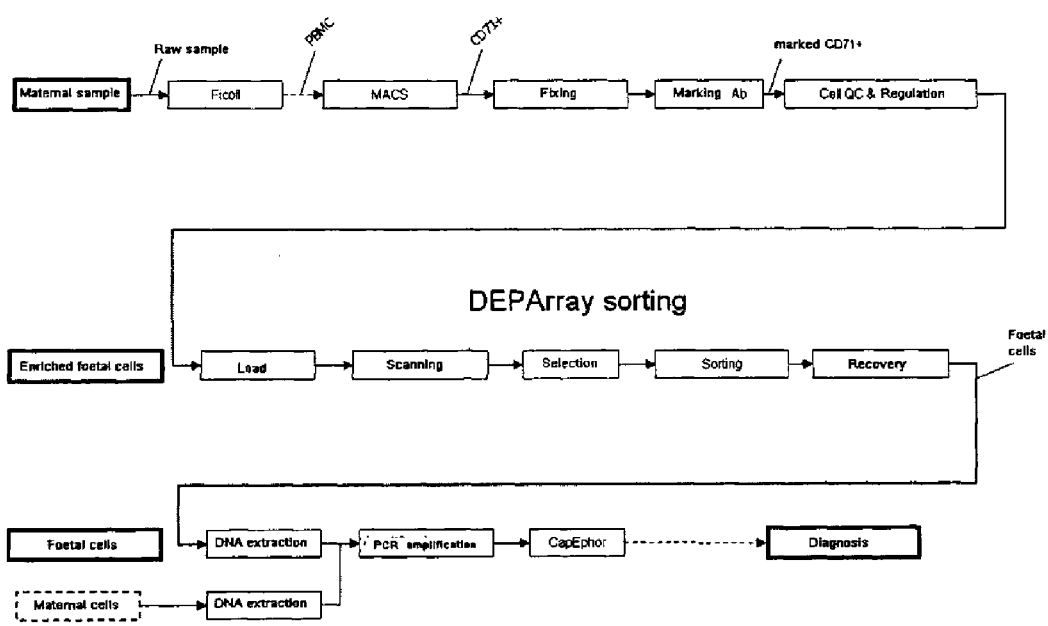

The sample is then loaded in a chip for the isolation of cells by means of mobile dielectrophoresis cages (DEPArray™ WO0069525, Silicon Biosystems SpA, for example as part of a package or overall device like the one schematically illustrated in FIG. 10) and undergoes scanning, identification and selection, sorting and recovery of the foetal cells. The caged cells are observed (scanning) automatically or manually under a microscope with three different fluorescence channels (or in three different wavelengths): in the non-limiting case described here, the blue channel allows verification of the presence of the nucleus and if necessary its morphology (e.g. marking with DAPI) and the green channel highlights the cells that have been marked with the specific foetal antibody which is conjugated with a fluorophore emitting in the green wavelength (e.g. FITC). According to one aspect of the invention, a third channel is also used, different from the first two (e.g. the channel emitting in the red wavelength, as for the filter used to detect the fluorescence of the TRITC), and for which no fluorescent marker has been used; this permits identification of the autofluorescent cells, for which any signal detected in the DAPI and green channels would not be specific.

Alternatively the third channel can be used to highlight cells conjugated with an antibody linked to a fluorophore, like for example the CD45, to identify the cells to be discarded.

Figure 2:
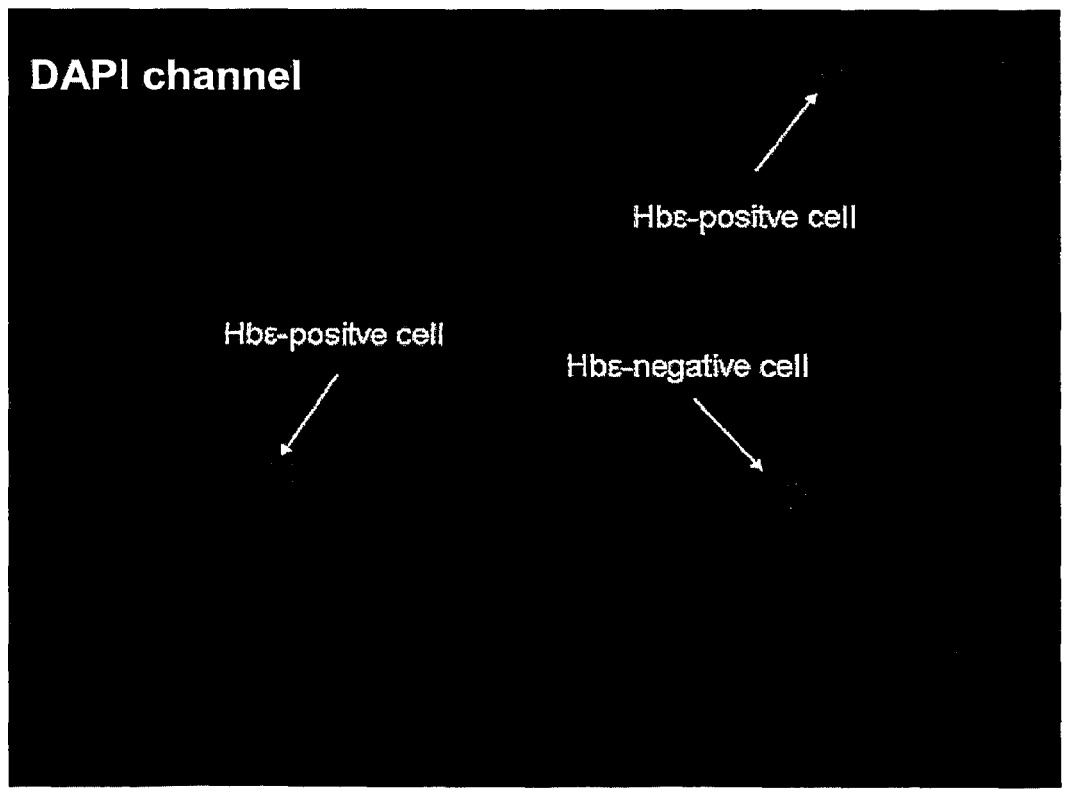
FIG. 2 shows an image of the chip with 10× magnification with filter for fluorescence of the DAPI. Three nuclei can be seen, corresponding to three single cells.
Figure 3:
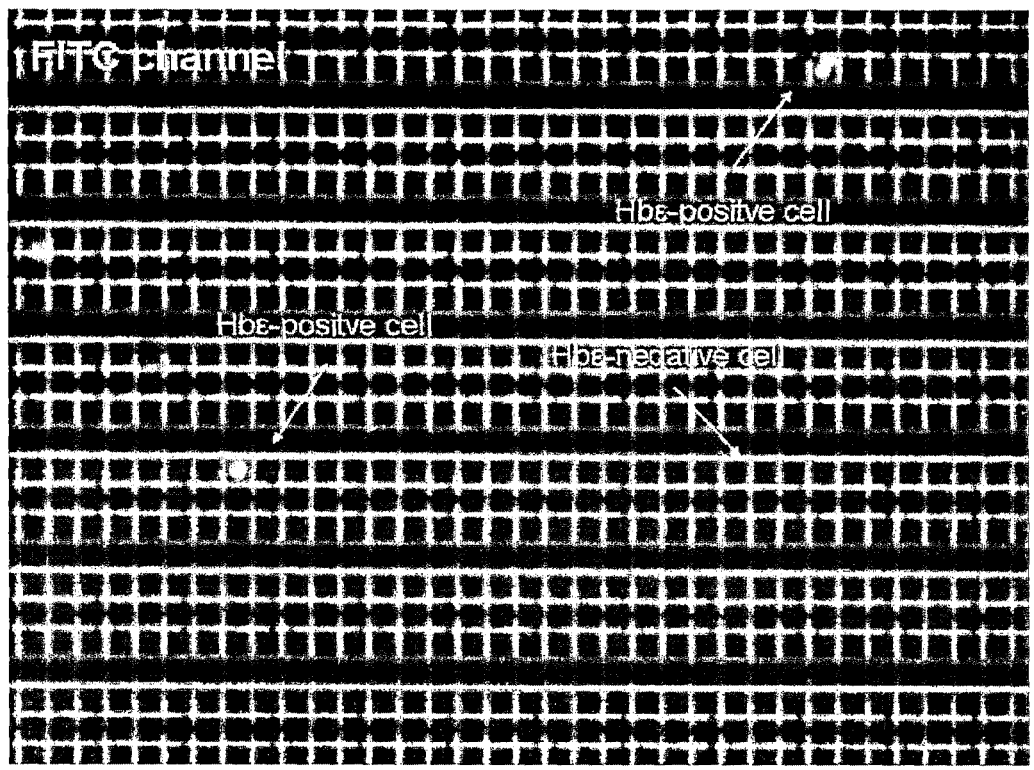
FIG. 3 shows an image of the chip with 10× magnification with filter for fluorescence of the FITC. The area photographed is the same as that of FIG. 2 and two Hb-e positive cells and one Hb-e negative cell can be seen.
Figure 4:
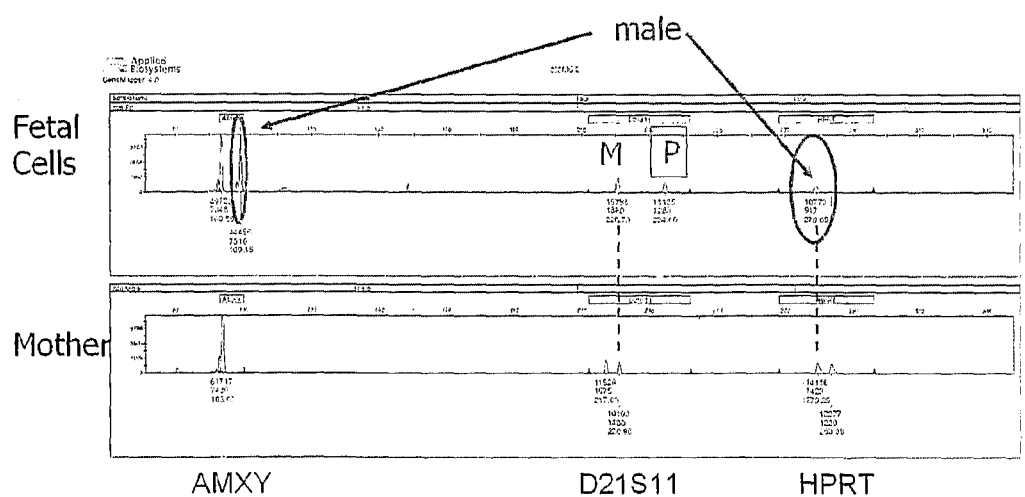
FIG. 4 shows an electropherogram relative to analysis of the chromosome marker AMXY, D21S11 and HPRT. The upper plot refers to the analysis performed on foetal cells recovered from maternal blood, the lower plot refers to the analysis performed on maternal cells. The graph shows the presence of the sex chromosomes X and Y in the foetus and at D21S11 the foetal cells have a first allele inherited from the mother (M) and a different second allele (of paternal origin (P)).
Figure 5:
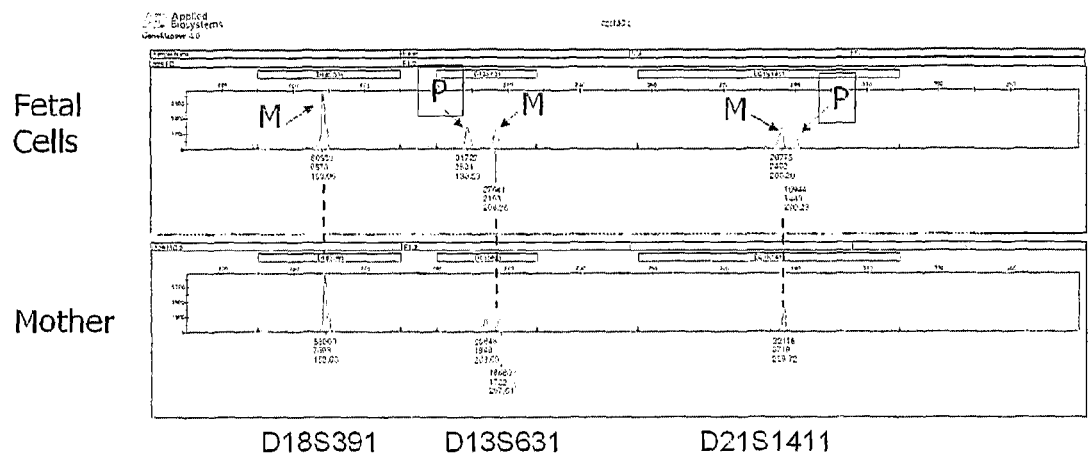
FIG. 5 shows an electropherogram relative to analysis of the chromosome markers D18S391, D13S631 and D21S1411. The upper plot refers to the analysis performed on the foetal cells recovered from maternal blood, the lower plot refers to the analysis performed on maternal cells. The graph shows for the markers D13S631 and D21S1411 the presence of two alleles (normal heterozygote) and contamination by maternal cells can be excluded.
Figure 6:
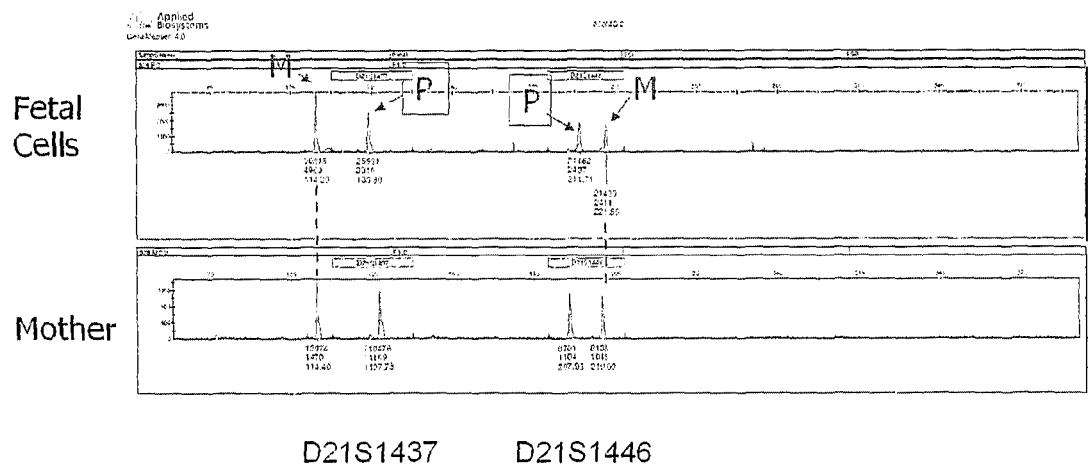
FIG. 6 shows an electropherogram relative to analysis of the marker D21S1437 and D21S1446. The upper plot refers to the analysis performed on foetal cells recovered from maternal blood, the lower plot refers to the analysis performed on maternal cells. The graph shows the presence of two alleles (normal heterozygote) and contamination by maternal cells can be excluded.
Figure 7:
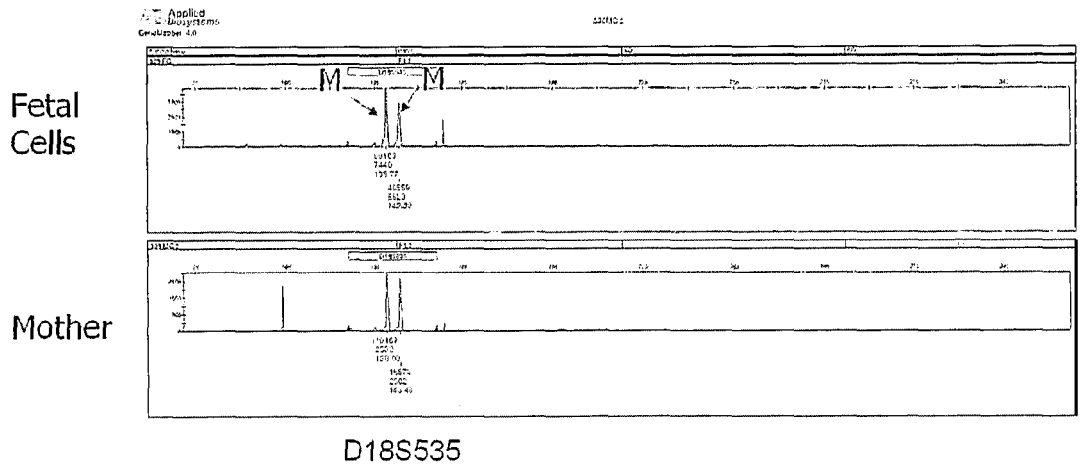
FIG. 7 shows an electropherogram relative to analysis of the marker D18S535. The upper plot refers to the analysis performed on foetal cells recovered from maternal blood, the lower plot refers to the analysis performed on maternal cells. The graph shows the presence of two no-call alleles (normal heterozygote).

The selection of cells is therefore made by selecting the cages that contain one single nucleated cell (positive to the DAPI, FIG. 2), which have a strong specific foetal antibody signal (positive to the FITC/Alexa, FIG. 3), and which have low or nil autofluorescence, detected on other channels (e.g. red channel).

To further improve the selectivity of the method, the fluorescent markers, in particular the foetal marker, instead of consisting of simple fluorescent molecules, can consist of fluorescent beads conjugated with antibody able to recognise the cells of interest, in this case the foetal cells.

The cells are recovered in a few microlitres (<40 microlitres) in a 0.2 millilitre PCR tube.

Genetic Analysis

From said cells thus obtained the DNA is extracted which is amplified and analysed for the presence of chromosomic aneuploidies, preferably operating in the same microfluidic device as the one used for the selection and, if necessary, already used previously for at least part of the enrichment process (for example in the case of use of the DACS technology); in this case the device can resemble the one illustrated in FIG. 10.

The equipment contains an array of electrodes as in the known art, but is characterised by a main microchamber (CHM) and a plurality of secondary microchambers (CHJ), all delimited on at least one face by one single chip or by a plurality of separate chips, bearing an array of electrodes that can be activated. The main microchamber can be filled with a sample comprising at least one cell via the relative inlets (IM1) and outlets (OM1). Each secondary microchamber (CHJ) is preferably of substantially greater dimensions but comparable to those of a cell. Preferably each secondary microchamber is connected to the main microchamber via a configuration channel (length and/or form) sufficient to forestall (prevent or at least limit) dispersion of the sample by diffusion and contamination towards other microchambers, in the time necessary for the analysis. According to the example illustrated, there is a plurality of secondary microchambers for the lysis connected to a channel for the capillary electrophoresis on chip, for example with cross joint. Alternatively a series of channels can be provided for the capillary electrophoresis with double T junction, according to the known art. Optionally, at the end of the channel for the capillary electrophoresis, there is an integrated sensor, of the impedentiometric and/or optical type, able to produce an electropherogram based on the migration time of the compounds analysed from the intersection (cross or double T) to the sensor itself. According to FIG. 10, in particular, each microchamber of the plurality of microchambers is connected to a capillary for the electrophoresis (CAPJ) via a fluidic outlet (OJ) of each secondary microchamber.

Extraction of the DNA of the recovered foetal cells is performed by alkaline thermolysis.

The determination of chromosome alterations is performed via analysis of the STR (Short Tandem Repeat) or microsatellites by means of QF-PCR. The technology of fluorescence capillary electrophoresis permits the simultaneous analysis of several STRs via the appropriate choice of fragments of DNA marked with different fluorescent molecules.

At least three different STRs, with high heterozygosis frequency in the population, of each of the chromosomes 13, 18 and 21 and three markers of the sex chromosomes are amplified in multiplex-PCR. In the case of a no-call, for example due to the presence of STR in homozygosis, a further STR of the same chromosome is amplified. The STRs analysed are: D21S11, D21S1410, D21S1411, D21S1412, D21S1435 and D21S1446 for analysis of the chromosome 21; D13S631, D13S634, D13S258, D13S305 and D13S742 for the chromosome 13; D18S535, D18S386, D18S391, D18S858 and D18S51 for the chromosome 18; for analysis of the sex chromosomes the markers AMXY and SRY, and the STR X22, DXYS218, DXS6803, DXS6809, DXS8377, HPRT and SBMA are analysed.

Parallel to amplification of the DNA of the foetal cells, the maternal DNA is analysed to recognise, according to one aspect of the invention, the presence of possible maternal contamination of the foetal cells or a possible external contamination of the QF-PCR (FIG. 4-7).

In the electropherograms, obtained from the capillary electrophoresis of the product of PCR with the automatic sequencer (for example with ABI prism 310), the areas and the dimensions of the peaks corresponding to the various alleles of the amplified microsatellites are analysed. Simultaneous analysis of the maternal DNA can help as a control to interpret the result of the genetic analysis, helping to identify possible cases of laboratory contaminations and contamination of the recovered foetal cells with maternal cells.

The genetic analysis phase can also be performed, according to a possible variation of the invention, by means of karyotype, in which case the phase of enrichment of at least one population of cells comprising at least one type of foetal nucleated cells furthermore comprises the phases of:
I. Blocking the Cells in Metaphase.

After stopping the cells in metaphase, fixing and permeabilisation are performed for identification of the foetal cells by means of an intra-cytoplasmatic antibody.

REFERENCES

[1] van Zwieten M C, Willems D L, Litjens L L, Schuring-Blom H G, Leschot N. How unexpected are unexpected findings in prenatal cytogenetic diagnosis? A literature review. Eur J Obstet Gynecol Reprod Biol. 2005 May 1; 120(1):15-21. Review.
[2] Nicolini U, Lalatta F, Natacci F, Curcio C, Bui T H. The introduction of QF-PCR in prenatal diagnosis of foetal aneuploidies: time for reconsideration. Hum Reprod Update. 2004 November-December; 10(6):541-8. Review.
[3] Leung W C, Lau E T, Lao T T, Tang M H. Rapid aneuploidy screening (FISH or QF-PCR): the changing scene in prenatal diagnosis? Expert Rev Mol Diagn. 2004 May; 4(3):333-7. Review.

[4] Hulten M A, Dhanjal S, Pertl B. Rapid and simple prenatal diagnosis of common chromosome disorders: advantages and disadvantages of the molecular methods FISH and QF-PCR. Reproduction. 2003 September; 126(3):279-97. Review.

[5] Adinolfi M, Pertl B, Sherlock J. Rapid detection of aneuploidies by microsatellite and the quantitative fluorescent polymerase chain reaction. Prenat Diagn. 1997 December; 17(13):1299-311. Review.

[6] Adinolfi M, Sherlock J. First trimester prenatal diagnosis using transcervical cells: an evaluation. Hum Reprod Update. 1997 July-August; 3(4):383-92. Review

[7] Bianchi D W, Simpson J L, Jackson L G, Elias S, Holzgreve W, Evans M I, Dukes K A, Sullivan L M, Klinger K W, Bischoff F Z, Hahn S, Johnson K L, Lewis D, Wapner R J, de la Cruz F. Foetal gender and aneuploidy detection using foetal cells in maternal blood: analysis of NIFTY I data. National Institute of Child Health and Development Foetal Cell Isolation Study. Prenat Diagn. 2002 July; 22(7):609-15.

[8] Shettles, L B (1971) Use of the Y chromosome in prenatal sex determination. Nature, 230, 52.

[9] Adinolfi, M, Davies, A, Sharif, S et al. (1993) Detection of trisomy 18 and Y-derived sequences in foetal nucleated cells obtained by transcervical flushing, Lancet, 342, 403-404.

[10] Adinolfi, M and Sherlock, J (1997) First trimester prenatal diagnosis using transcervical cells: an evaluation, Human Reproduction Update, 3 (4), 383-392.

[11] Miller, D, Briggs, J, S. Rahman, M, et al. (1999) Transcervical recovery of foetal cells from the lower uterine pole: reliability of recovery and histological/immunocytochemical analysis of recovered cell populations, Human Reproduction, 14 (2), 521-531

[12] Bussani, C, Cioni, R, Scarselli B, et al. (2002) Strategies for the isolation and detection of foetal cells in transcervical samples, Prenatal Diagnosis, 22, 1098-1101.

[13] Bussani, C, Scarselli, B, Cioni, R, et al. Use of the quantitative fluorescent-PCR assay in the study of foetal DNA from micromanipulated transcervical samples, Mol Diagn, 8 (4), 259-263

[14] Wang J Y, Zhen D K, Falco V M, Farina A, Zheng Y L, Delli-Bovi L C, Bianchi D W. Foetal nucleated erythrocyte recovery: fluorescence activated cell sorting-based positive selection using anti-gamma globin versus magnetic activated cell sorting using anti-CD45 depletion and anti-gamma globin positive selection. Cytometry. 2000 Mar. 1; 39(3):224-30.

[15] Samura O, Sekizawa A, Zhen D K, Falco V M, Bianchi D W. Comparison of foetal cell recovery from maternal blood using a high density gradient for the initial separation step: 1.090 versus 1.119 g/ml. Prenat Diagn. 2000 April; 20(4):281-6.

[16] Sekizawa A, Farina A, Zhen D K, Wang J Y, Falco V M, Elmes S, Bianchi D W. Improvement of foetal cell recovery from maternal blood: suitable density gradient for FACS separation. Foetal Diagn Ther. 1999 July-August; 14(4): 229-33.

[17] Sekizawa A, Samura O, Zhen D K, Falco V, Bianchi D W. Foetal cell recycling: diagnosis of gender and RhD genotype in the same foetal cell retrieved from maternal blood. Am J Obstet Gynecol. 1999 November; 181(5 Pt 1):1237-42.

[18] Zheng Y L, Zhen D K, DeMaria M A, Berry S M, Wapner R J, Evans M I, Copeland D, Williams J M, Bianchi D W. Search for the optimal foetal cell antibody: results of immunophenotyping studies using flow cytometry. Hum Genet. 1997 July; 100(1):35-42.

[19] Geifman-Holtzman O, Bernstein I M, Berry S M, Holtzman E J, Vadnais T J, DeMaria M A, Bianchi D W. Foetal RhD genotyping in foetal cells flow sorted from maternal blood. Am J Obstet Gynecol. 1996 March; 174(3):818-22.

[20] Bianchi D W, Klinger K W, Vadnais T J, Demaria M A, Shuber A P, Skoletsky J, Midura P, Diriso M, Pelletier C, Genova M, Erikson M S, Williams J M. Development of a model system to compare cell separation methods for the isolation of foetal cells from maternal blood. Prenat Diagn. 1996 April; 16(4):289-98.

[21] DeMaria M A, Zheng Y L, Zhen D, Weinschenk N M, Vadnais T J, Bianchi D W. Improved foetal nucleated erythrocyte sorting purity using intracellular antifoetal hemoglobin and Hoechst 33342. Cytometry. 1996 Sep. 1; 25(1):37-45.

[22] Zheng Y L, Craigo S D, Price C M, Bianchi D W. Demonstration of spontaneously dividing male foetal cells in maternal blood by negative magnetic cell sorting and fish. Prenat Diagn. 1995 June; 15(6):573-8.

[23] Zheng Y L, Demaria M, Zhen D, Vadnais T J, Bianchi D W. Flow sorting of foetal erythroblasts using intracytoplasmic anti-foetal haemoglobin: preliminary observations on maternal samples. Prenat Diagn. 1995 October; 15(10): 897-905.

[24] Bianchi D W, Yih M C, Zickwolf G K, Flint A F. Transferrin receptor (CD71) expression on circulating mononuclear cells during pregnancy. Am J Obstet Gynecol. 1994 January; 170(1 Pt 1):202-6.

[25] Bianchi D W, Shuber A P, DeMaria M A, Fougner A C, Klinger K W. Foetal cells in maternal blood: determination of purity and yield by quantitative polymerase chain reaction. Am J Obstet Gynecol. 1994 October; 171(4):922-6.

[26] Bianchi D W, Mahr A, Zickwolf G K, Houseal T W, Flint A F, Klinger K W. Detection of foetal cells with 47, XY, +21 karyotype in maternal peripheral blood. Hum Genet. 1992 December; 90(4):368-70.

[27] Bianchi D W, Stewart J E, Garber M F, Lucotte G, Flint A F. Possible effect of gestational age on the detection of foetal nucleated erythrocytes in maternal blood. Prenat Diagn. 1991 August; 11(8):523-8.

[28] Reichle C, Sparbier K, Muller T, Schnelle T, Walden P and Fuhr G, Electrophoresis, 2001; 22:272-82.

[29] Fiedler S, Shirley S G, Schnelle T and Fuhr G, Anal. Chem. 1998; 70:1909-15.

[30] Enger J, Goksor M, Ramser K, Hagberg P and Hantstorp D, Lab Chip, 2004; 4:196-200.

[31] Manaresi N, Romani A, Medoro G, Altomare L, Leonardi A, Tartagni M and Guerrieri R, IEEE J. Solid-State Circuits, 2003; 38:2297-2305.

[32] Romani A, Manaresi N, Marzocchi L, Medoro G, Leonardi A, Altomare L, Tartagni M and Guerrieri R, Proceedings of the International Solid State Circuit Conference, 2004; 1:224-225.

The invention claimed is:

1. A method for non-invasive pre-natal diagnosis, comprising:
   a. obtaining a sample of an organic fluid having a high probability of containing fetal nucleated cells from a pregnant woman;
   b. enriching at least one population of cells in the sample of organic fluid, the at least one population of cells comprising at least one type of fetal nucleated cells;

c. marking the fetal nucleated cells with a specific antibody for the fetal nucleated cells capable of discriminating the fetal nucleated cells from maternal cells in the sample of organic fluid;
d. marking the fetal nucleated cells of the sample with a marker specific for a cell nucleus, the marker specific for the cell nucleus being distinguishable from the specific antibody, wherein both the specific antibody and the marker specific for a cell nucleus each comprise a fluorescent marker, the fluorescent marker of the specific antibody having emission in a first wavelength, and the fluorescent marker of the marker specific for a cell nucleus having emission in a second wavelength, the first and second wavelengths being different from each other;
e. isolating at least one cell from among said at least one type of fetal nucleated cells by individually selecting single cells marked with the specific antibody using a microfluidic device for the selection of single cells, wherein isolating at least one fetal nucleated cell comprises detecting emission of a third wavelength generated by autofluoresences by said cells in said sample of said organic fluid and individually selecting only single cells that emit in the first and second wavelengths but which, at the same time, do not emit in said third wavelength; and
f. performing a genetic analysis on said at least one fetal nucleated cell isolated from among said at least one type of nucleated cells in order to highlight at least one genetic characteristic of said at least one fetal nucleated cell suitable for permitting said pre-natal diagnosis.

2. The method as claimed in claim 1, wherein individually selecting single cells marked with the specific antibody using a microfluidic device comprises capturing single cells, each at a specific site of a plurality of sites of the microfluidic device positioned in the microfluidic device according to an array, and selecting from among the cells captured the single cells on the basis of at least one parameter which can be detected by means of a sensor internal or external to the microfluidic device.

3. The method as claimed in claim 1, wherein enriching said sample of said organic fluid comprises selecting cells on the basis of at least one parameter selected from the group consisting of:
 a. density;
 b. morphology;
 c. electrical properties;
 d. chemical properties;
 e. mechanical properties;
 f. expression of surface antigens;
 g. expression of intra-cytoplasmatic antigens;
 h. dielectric properties;
 i. magnetic properties;
 and combinations of the same.

4. The method as claimed in claim 3, wherein enriching said sample of said organic fluid in at least one population of cells comprising at least one type of fetal nucleated cells comprises treating said sample of said organic fluid in order to separate nucleated cells and consequently enrich the sample in nucleated cells.

5. The method as claimed in claim 4, wherein treating the sample of said organic fluid in order to separate the nucleated cells and consequently enrich it in nucleated cells comprises centrifuging said sample of said organic fluid on a density gradient.

6. The method as claimed in claim 1, wherein enriching the sample of organic fluid comprises selecting cells on the basis of at least one of the following characteristics of said population of cells comprising at least one type of fetal nucleated cells:

a. expression of the surface antigen CD71;
 b. expression of the surface antigen CD34;
 c. expression of the surface antigen GPA;
 d. absence of expression of the surface antigen CD14;
 e. absence of expression of the surface antigen CD15; and
 f. absence of expression of the surface antigen CD45.

7. The method as claimed in claim 1, further comprising diluting said sample of said organic fluid after said step of enrichment and before said step of isolation of at least one cell from among said at least one type of fetal nucleated cells; wherein said dilution is performed on the basis of a count of a number of nucleated cells present in a portion of pre-established volume of said sample, which is separated from the sample of said organic fluid after said enrichment step.

8. The method as claimed in claim 1, wherein at least one or both said steps of enriching and performing a genetic analysis are carried out within the same microfluidic device for performing the isolating step.

9. The method as claimed in claim 8, wherein the microfluidic device is provided with a plurality of different chambers, separated from one another and hydraulically connected, delimited on at least one face by one single chip or by a plurality of separate chips.

10. The method as claimed in claim 1, wherein marking of the fetal nucleated cells with a the specific antibody for the fetal nucleated cells suitable for discriminating them from the maternal cells is performed by using a variety of antibodies directed against a specific antigen selected from the group consisting of:
 antibodies that recognize fetal trophoblast antigens,
 antibodies that recognize fetal surface antigens and,
 antibodies that recognize intracellular antigens.

11. The method as claimed in claim 10, wherein said specific antibody for the fetal nucleated cells suitable for discriminating them from the maternal cells is or has a fluorescent marker.

12. The method as claimed in claim 10, wherein said specific antibody for the fetal nucleated cells suitable for discriminating them from the maternal cells is conjugated with a fluorescent bead.

13. The method as claimed in claim 10, further comprising fixing and permeabilizing the cells for identification of the fetal nucleated cells by means of an intra-cytoplasmatic antibody after marking the fetal nucleated cells.

14. The method as claimed in claim 1, wherein genetic analysis is performed by means of QF-PCR and comprises comparing genetic information carried by said at least one fetal nucleated cell to genetic information carried by at least one maternal nucleated cell.

15. The method as claimed in claim 1, further comprising placing in a culture the sample of enriched organic fluid and repeating on said sample of enriched organic fluid after having placed it in a culture, the enriching step.

16. The method as claimed in claim 1, wherein said sample of an organic fluid contains cells selected from the group consisting of uterine cells, transcervical cells, endocervical cells, and peripheral maternal blood cells.

17. The method as claimed in claim 1, wherein said microfluidic device for the selection of single cells is a disposable device.

18. The method of claim 10, wherein the fetal trophoblast antigen is HLA-G.

19. The method of claim 10, wherein the fetal surface antigens are i-antigens.

20. The method of claim 10, wherein the intracellular antigens are hemoglobin chains Y and $\in$.

* * * * *

UNITED STATES PATENT AND TRADEMARK OFFICE
CERTIFICATE OF CORRECTION

PATENT NO. : 8,383,341 B2
APPLICATION NO. : 12/598881
DATED : February 26, 2013
INVENTOR(S) : Nicolò Manaresi et al.

It is certified that error appears in the above-identified patent and that said Letters Patent is hereby corrected as shown below:

Title Page, item (75) Inventors:

Nicolò Manaresi, "Milan, (IT)" should read –

Nicolò Manaresi, "Bologna, (IT)"

Antonio Fittipaldi, "Bologna, (IT)" should read –

Antonio Fittipaldi, "Milano, (IT)"

In the Drawings:

Drawing Sheet 1 of 5, delete FIG. 1 and substitute therefore with the FIG. 1 on attached page Drawing Sheet 4 of 5, delete FIG. 8 and substitute therefore with the FIG. 8 on attached page Signed and Sealed this
Ninth Day of December, 2014

Michelle K. Lee
*Deputy Director of the United States Patent and Trademark Office*